United States Patent [19]

Itoh et al.

[11] 4,406,525

[45] Sep. 27, 1983

[54] LIGHT BEAM SCANNING DEVICE

[75] Inventors: Kiyoshi Itoh, Fukuoka; Tetuo Kamoshita, Toda, both of Japan

[73] Assignee: Asahi Kogaku Kogyo Kabushiki Kaisha, Tokyo, Japan

[21] Appl. No.: 205,024

[22] Filed: Nov. 7, 1980

[30] Foreign Application Priority Data

Nov. 19, 1979 [JP] Japan ............................... 54-149782

[51] Int. Cl.³ .......................................... G05D 25/00
[52] U.S. Cl. ..................................... 350/486; 356/138
[58] Field of Search ............... 350/486; 356/399, 153, 356/138; 128/303.1, 395

[56] References Cited

U.S. PATENT DOCUMENTS

| | | | |
|---|---|---|---|
| 3,487,835 | 1/1970 | Koester et al. | 128/395 |
| 3,796,220 | 3/1974 | Bredemeier | 128/303.1 |
| 3,828,788 | 8/1974 | Krasnov et al. | 128/303.1 |
| 4,091,814 | 5/1978 | Togo | 128/303.1 |

*Primary Examiner*—R. A. Rosenberger
*Attorney, Agent, or Firm*—Sughrue, Mion, Zinn, Macpeak, and Seas

[57] ABSTRACT

A small size and lightweight light beam scanning device for scanning a laser beam to perform an operation under an operating microscope. A movable mirror is provided which occupies only a small central portion of the objective lens of the microscope. Horizontal rotary shafts are provided on an annular pivot frame outside the field of vision of the objective lens. Rotational movement around the horizontal axis is transmitted vertically downwardly from the center of the movable mirror by a lever mechanism. A vertical bearing mechanism permits the movable mirror to turn around the vertical axis together with the lever mechanism. Rotational movement around the vertical and horizontal axes is transmitted through a universal joint to a gimbal system operating lever by a single lever.

6 Claims, 6 Drawing Figures

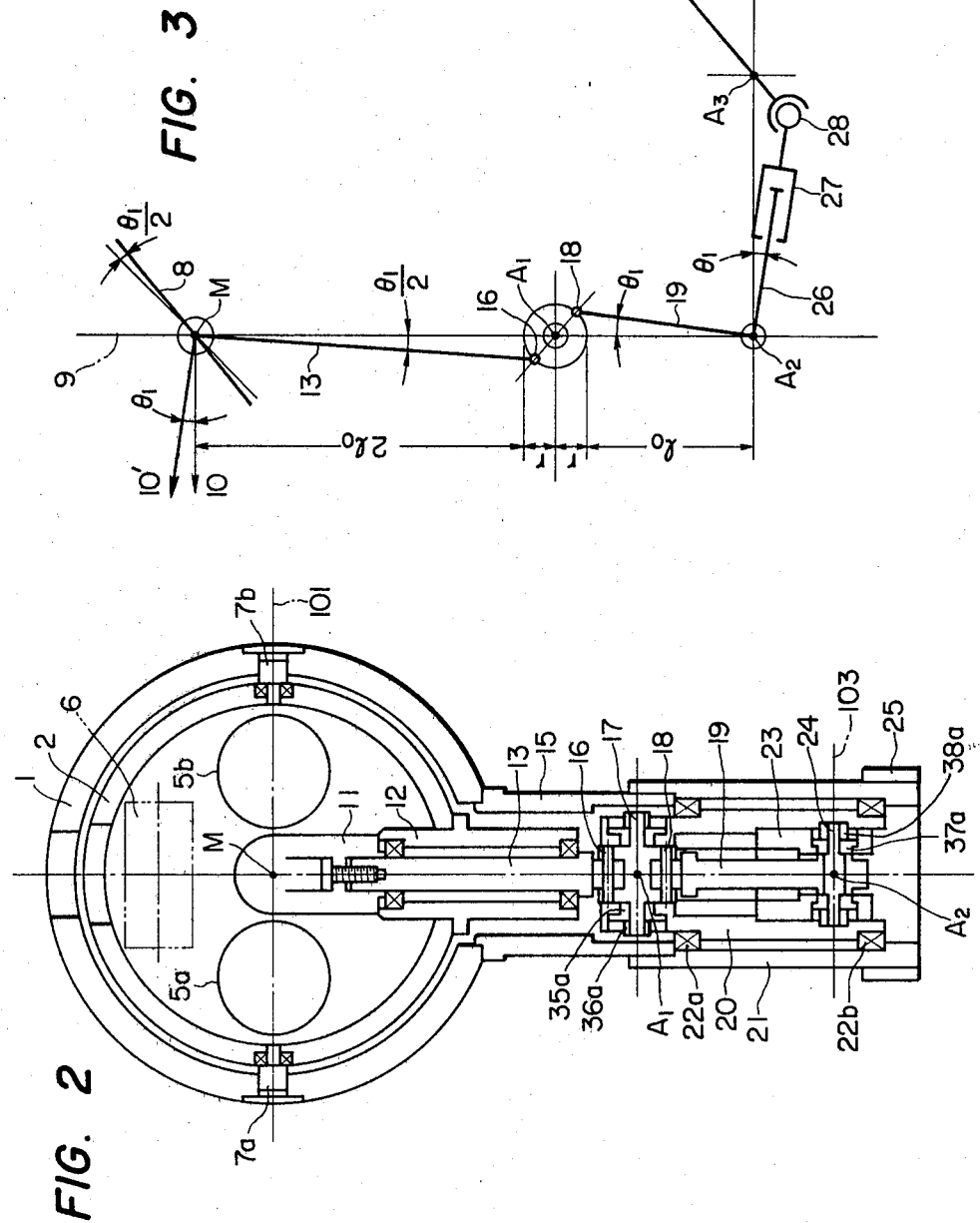

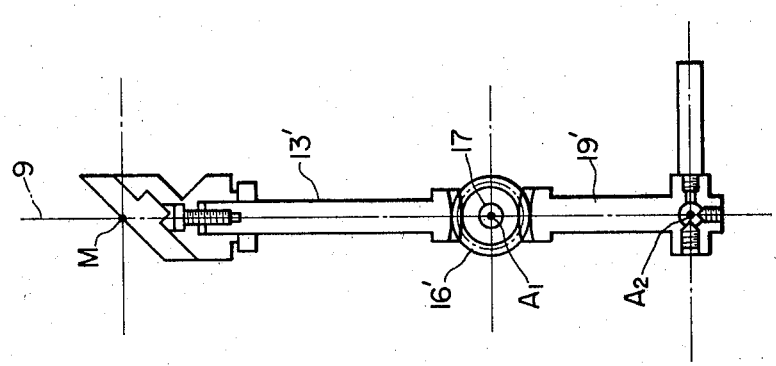
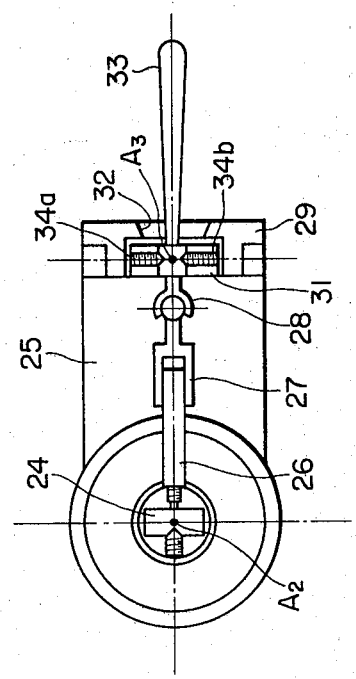
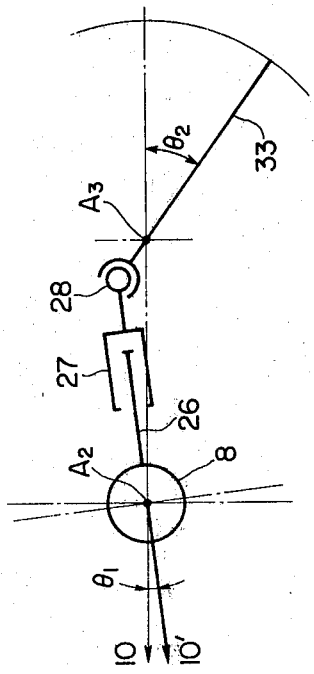

LIGHT BEAM SCANNING DEVICE

BACKGROUND OF THE INVENTION

The present invention relates to a light beam scanning device for scanning a laser beam in an application where a delicate and precise operation is to be carried out with the laser beam under an operating microscope.

To perform a delicate and precise operation on the human body with a laser knife, in general, a light beam scanning device incorporating a movable mirror is mounted on the front part of an operating microscope and a laser beam is reflected by the movable mirror into the field of vision of the microscope to illuminate the desired location. In order to direct the laser beam to a desired point in the field of vision, it is necessary to scan the laser beam by slightly turning the movable mirror vertically or horizontally. In general, the movable mirror is disposed on the optical axis of the objective lens of the operating microscope and in front of the objective lens forming an angle of 45° with the optical axis. After being reflected by the movable mirror, the incident laser beam advances along the optical axis to the desired point of illumination.

On the other hand, it is necessary for the operator to locate the part to be operated on in the field of vision of the microscope at all times and hence the laser beam must be collimated and accurately applied. Moreover, the movable mirror should not obstruct the field of vision.

The right and left sides of the circular field of vision of the objective lens of the microscope are filled by the rays which form the fields of vision of the right and left eyepieces of the microscope, respectively, and the upper part of the circular field of vision of the objective lens is used to apply light for illuminating the field of vision. Accordingly, in the field of vision of the objective lens, only the central part and a slit-shaped part below the center are available for the reflection of the laser beam.

Taking these facts into account, movable mirrors have been designed having various configurations and dimensions. A conventional movable mirror is provided with a transparent glass plate large enough to cover the diameter of the objective lens. The central portion of the transparent glass plate is formed as a small circular portion on which a metal film is deposited by vacuum evaporation with the circular portion being large enough to reflect a laser beam. Such a movable mirror, which is necessarily large in size, is supported by a mirror supporting frame which includes a mechanism for rotating the mirror around the horizontal and vertical axes thereof. Accordingly, the mirror supporting frame must be larger than the movable mirror. The rotating mechanism is, in general, a gimbal mechanism and the movable mirror is turned by operating an operating lever which is rotatable around the gimbal fulcrum.

In such a light beam scanning device, the space in front of the objective lens is occupied by the large movable mirror and therefore the gimbal part is disposed at the righthand side in the housing of the device. Accordingly, the device is quite long in the widthwise direction.

Light beam scanning devices of this type have been disclosed by Japanese Laid-Open Patent Application Nos. 8085/1974 and 8997/1979.

It is desirable to reduce the size and weight of the device by decreasing both the width and depth as much as possible due to the following reasons. An operation using a laser beam under microscope is often carried out with the aid of an endoscope extended to the part to be operated on. The focal distance of the objective lens of the device ranges from 200 mm to 400 mm. However, it is desirable that the distance between the objective lens and the incidence end of the endoscope be long enough to facilitate the operation. The endoscope requires a minimum length to be suitable for performing most operations. Accordingly, the depth of the light beam scanning device, namely, the thickness in the direction of the optical axis, must be made as small as possible. Furthermore, the width of the device should be as small as possible because the spaces on the right-hand side and left-hand side of the objective lens are used to carry out auxiliary operations during the operation.

Accordingly, an object of the invention is to provide a light beam scanning device small in size and light in weight in which its movable mirror is so dimensioned as not to obstruct observation through an operating microscope and the illumination range of the microscope, its width and depth are so small that the device does not obstruct an operation, and the rotational movement of the movable mirror around any one or both of the horizontal and vertical axes is smoothly carried out without interference.

SUMMARY OF THE INVENTION

In order to achieve this object, the light beam scanning device according to the invention is provided with the following structure.

The movable mirror occupies only a small central portion of the objective lens. That is, it is so dimensioned as not to obstruct the field of vision of the objective lens. Horizontal rotary shafts are provided on an annular pivot frame outside the field of vision of the objective lens. Rotational movement around the horizontal axis is transmitted vertically downwardly from the center of the movable mirror by a lever mechanism.

A vertical bearing mechanism is provided to allow the movable mirror to turn around the vertical axis together with the lever mechanism. That is, as the device is so designed that rotational movement of the movable mirror around the horizontal and vertical axes is transmitted vertically downwardly, the device is small both in width and depth.

Rotational movement around the two axes is integrally transmitted through a universal joint to a gimbal system operating lever by a single lever. Therefore, the two types of rotational movement are smoothly achieved with a simple mechanism without interference.

BRIEF DESCRIPTION OF THE DRAWINGS

FIGS. 1 and 2 are, respectively, a sectional side elevation and a sectional front elevation of a preferred embodiment of a light beam scanning device constructed according to the present invention;

FIGS. 3 and 5 are explanatory diagrams showing, respectively, the rotational operations of a movable mirror around the horizontal axis and the vertical axis;

FIG. 4 is a horizontal sectional view of a gimbal mechanism used with the invention; and FIG. 6 is a diagram showing another example of a mechanism for transmitting rotational movement around the horizontal axis of the mirror which may be used in the device of FIGS. 1 and 2.

DESCRIPTION OF THE PREFERRED EMBODIMENTS

Figure 1:
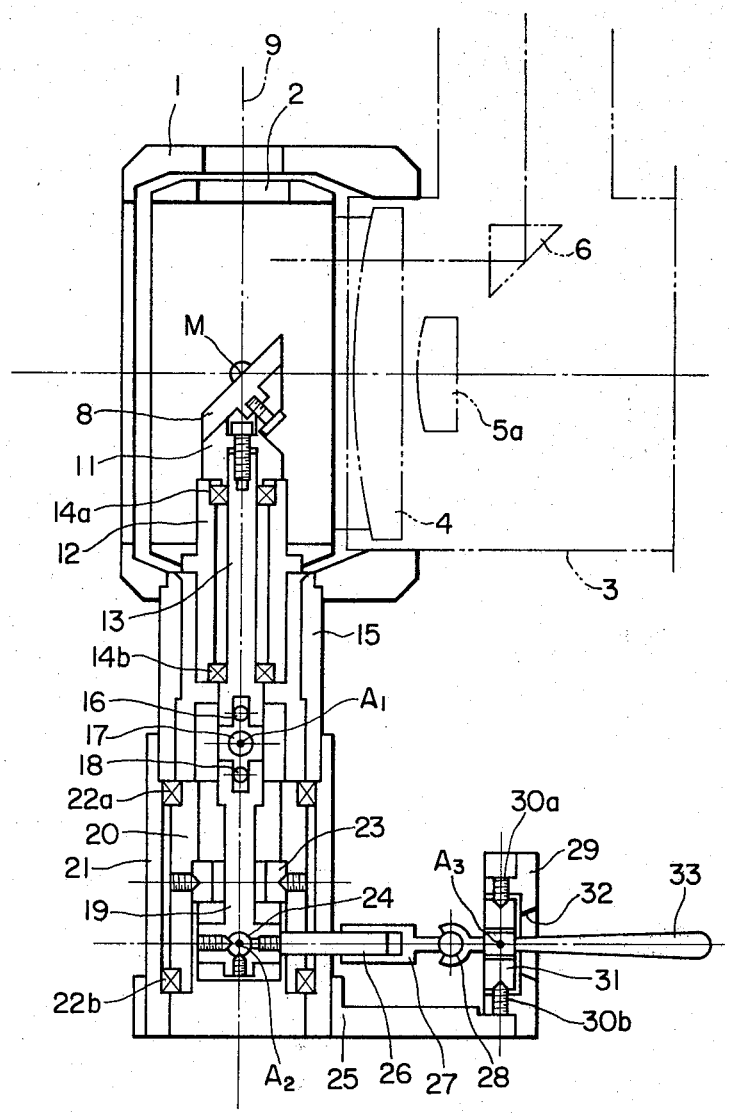

A preferred embodiment of the present invention will be described with reference to the accompanying drawings.

FIGS. 1 and 2 are a sectional side elevation view and a sectional front elevation view of a light beam scanning device constructed according to the invention, respectively. The device of the invention includes a housing, a movable mirror, a rotary mechanism rotatable around a vertical axis of the movable mirror, a rotary mechanism rotatable around a horizontal axis of the movable mirror, a rotational movement transmitting mechanism, and a gimbal mechanism, that is, an operating section.

The housing is constituted by a pivot holder 1, a first outer cylinder 15, a second outer cylinder 21 and a supporting arm 25 which are secured to one another to form an integral unit. The pivot holder 1 is secured to a lens barrel in front of the objective lens 4 of an operating microscope 3 and it is so adjusted that the optical axis of a movable mirror 8 coincides with that of the operating microscope 3.

The relationship between the field of vision of the microscope 3 and the set position and dimensions of the movable mirror 8 are as follows with reference to FIGS. 1 and 2. Relay lenses 5a and 5b corresponding respectively to the fields of vision of the right and left eyepieces are disposed behind the objective lens 4. A field-of-vision illuminating prism 6 is disposed behind and above the objective lens 4. The movable mirror 8 is so dimensioned as not to obstruct the three effective fields of vision. The center M of the movable mirror 8 is on the optical axis of the objective lens 4. A narrow gap-shaped portion extends vertically downwardly from the center of the movable mirror 8. That portion is used to accommodate a link mechanism adapted to transmit rotational movement around the horizontal axis.

The rotary mechanism positioned around the horizontal axis of the movable mirror 8 is constructed as follows. A pair of pivots 7a and 7b are secured to the pivot holder 1 on a horizontal axis 101 passing through the center M of the movable mirror 8. A pivot frame 2 is suspended from the pivots 7a and 7b through bearings. The movable mirror 8 is held by a mirror holder 11 which is secured to a first lever 13. The first lever 13 is so arranged that it can turn around the vertical axis of the movable mirror 8 through bearings 14a and 14b which are provided in a third outer cylinder 12. As the third outer cylinder 12 is fixedly secured to the pivot frame 2, the movable mirror 8 can rock around the horizontal axis 101. Thus, the movable mirror 8 can turn around both the horizontal and vertical axes simultaneously.

The mechanism for transmitting rotational movement around the horizontal axis is constructed as follows. A hollow shaft 20 is rotatably mounted around the vertical axis. A rotary shaft 17 is coupled to the hollow shaft 20 with flanged bearings 35a and 36a. The rotary shaft 17 has two fork-shaped end portions in which pins 16 and 18 are fitted, respectively. These portions will be referred to as "a direction changing mechanism" hereinafter. The function of this mechanism will be described below with reference to FIG. 3. The mechanism is used to make the direction of rotation of an operating lever coincide with the direction of deflection of a laser beam reflected by the movable mirror 8.

The first lever 13 has a fork at the lower end which is engaged with the pin 16. The pin 18 is engaged with a second lever 19. The second lever 19 has a rotary shaft 24 which is coupled to the hollow shaft 20 with flanged bearings 37a and nuts 38a. Therefore, the rotational or rocking motion of the second lever 19 around the rotary shaft is transmitted through the pins 16 and 18 to the first lever 13 so that the movable mirror 8 is correspondingly turned or rocked around the horizontal axis. A holder 23 supports the flanged bearings 37a and the rotary shaft 24.

The hollow shaft 20 and the second outer cylinder 21 are fitted into the inner and outer races of bearings 22a and 22b, respectively. Therefore, the hollow shaft 20 and the second lever 19 can turn around the vertical axis in association with the first lever 13. A specific feature of the invention resides in that, as described above, the rotational movements around the horizontal and vertical axes of the movable mirror 8 are simultaneously transmitted downwardly.

The above-described mechanism for transmitting rotational movement around the horizontal axis may be replaced by a different mechanism if desired. In the mechanism described above, the direction changing mechanism is coupled to the first and second levers through engagement of the forks and tube. However, they may be coupled by employing a gear engaging system or a roller engaging system. FIG. 6 shows another example of a mechanism for transmitting rotational movement around the horizontal axis. In this example, the motion transmitting portions of a first fork 13' and a second fork 19' are provided as sector-shaped gears which turn around centers M and $A_2$, respectively, and the direction changing mechanism is a pinion 16' which has a rotating center $A_1$. Instead of the sector-shaped gears and the pinion, semi-circular rollers and a roller may be employed thereby providing a rotational movement transmitting mechanism utilizing frictional surfaces.

Next, the gimbal mechanism including the operating lever will be described. An intermediate lever 26 extends in a direction which passes through the fulcrum $A_2$ of the second lever 19 perpendicular to its center line and its horizontal axis 103. The intermediate lever 26 is fixedly secured to the second lever 19. A sleeve 27 extending from the inner ball of a universal joint 28 is disposed on the right-hand side of the intermediate lever 26. The intermediate lever 26 is engaged with the sleeve 27. The outer ball of the universal joint 28 is fixedly secured to the operating lever 33 so that the lever 33 can rock around the gimbal fulcrum $A_3$. A gimbal holder 29 is secured to the supporting arm 25 which is fixedly mounted on the second outer cylinder 21. Pivots 30a and 30b are mounted directly opposite one another on a vertical axis passing through the gimbal fulcrum $A_3$ on which is mounted a gimbal member 31.

The rotational movement of the operating lever 33 around the horizontal axis will be described with reference to FIG. 4 which is a horizontal sectional view of the gimbal mechanism. Pivots 34a and 34b are attached to the gimbal member 31 on a horizontal axis passing through the gimbal fulcrum $A_3$ suspended the operating lever 33. Thus, the operating lever 33 can undergo conical motion around the gimbal fulcrum $A_3$. This motion is transmitted through the intermediate lever 26 to the second lever 19 so as to turn the movable mirror 8 around the horizontal and vertical axes.

FIG. 3 shows the rotational operation of the movable mirror around the horizontal shaft. When the operating lever 33 is turned through an angle $\theta_2$ upwardly, the rotational movement is transmitted as indicated in FIG. 3. The second lever 19 is accordingly turned to the right by an angle $\theta_1$. After the direction of rotation is changed by the direction changing mechanism, the first lever 13 is turned to the left by an angle $\theta_1/2$. The first lever 13 has a length of $2l_0$ where $l_0$ is the length of the second lever 19. Accordingly, the movable mirror 8 is turned clockwise by an angle $\theta_1/2$. At the same time, a laser beam 10 applied from above the vertical axis 9 is deflected through the angle $\theta_1$ by the movable mirror 8 forming a laser beam 10'. As is apparent from FIG. 3, both the direction of movement of the operating lever and the direction of deflection of the laser beam are upward. This is important in terms of human engineering consideration. That is, it is essential that when the operator operates the operating lever 33 to scan the laser beam, the directions of movement of the operating lever and the laser beam remain relatively constant which makes it necessary to provide the direction changing mechanism. If the distance between the ball center of the universal joint 28 and the gimbal fulcrum is made shorter than the length of the intermediate lever 26, the operating accuracy of the lever 33 will be increased.

FIG. 5 shows the rotational operation of the movable mirror around the vertical axis. When the operating lever 33 is turned through an angle $\theta_2$ to the left, the rotational movement is transmitted as shown in FIG. 5. That is, the movable mirror 8 is turned by an angle $\theta_1$ to the left and accordingly the reflected laser beam 10' is deflected by the same angle $\theta_1$. In this case also, the lever operation direction is the same as the laser beam deflection direction. As is apparent from the above description, as the operating lever is swung through an angle $\theta_2$ vertically or horizontally, the laser beam is deflected by an angle $\theta_1$ in the same direction. The ratio of angles $\theta_2/\theta_1$ represents a manipulation sensitivity.

In FIGS. 1 and 4, a circular hole 32 formed in the gimbal holder 29 is provided to control the circular scanning range of the laser beam.

Thus, the objects of the invention have been achieved without separating the horizontal and vertical operations of the laser beam reflecting mirror unlike the structure described in Japanese Laid-Open Patent Application No. 8085/1974 and without using the electrical means for performing the desired operations unlike that described in Japanese Laid-Open Patent Application No. 8997/1979. The specific features of the invention have become clear from the above description.

The light beam scanning device according to the invention has a wide range of applications. That is, it can be utilized not only for microsurgery using a laser knife, but also as a micromanipulator for precision laser machining. In the above description, the device of the invention is used to scan a laser beam. However, the invention is not limited thereto or thereby. That is, it can, for instance, be used to scan a light beam emitted by an ordinary light source.

What is claimed is:

1. A light beam scanning device comprising:
   a movable mirror positioned on an optical axis of an objective lens in an operating microscope;
   a mirror holder attached to said movable mirror for holding said movable mirror, said mirror holder being rotatable around a vertical and a horizontal axis passing through a center of said movable mirror, said mirror holder being smaller than said objective lens and being dimensioned so that light rays passing through said objective lens and forming an effective field of vision of said microscope pass outside an outer perimeter of said mirror holder;
   an outer cylinder having one end disposed adjacent to said mirror holder;
   a pivot frame fixedly secured to said outer cylinder in such a manner as to be rotatable around said horizontal axis passing through said center of said movable mirror;
   a pivot holder holding said pivot frame; and
   means for rotating said mirror holder around said horizontal and vertical axis so as to rotate said mirror and reflect an incident light beam in a desired direction.

2. The device as claimed in claim 1 wherein said rotating means comprises a first lever coupled to said mirror holder and a second lever coupled to said first lever, said first and second levers each being rotatable around said vertical axis and separate horizontal axes, a link mechanism, said first and second levers being coupled to each other through said link mechanism, and a third lever, said third lever extending through and being perpendicular to said horizontal and said vertical axes of said second lever, said mirror holder being rotatable by operating said third lever.

3. The device as claimed in claim 2 wherein said link mechanism for coupling first and second levers to each other comprising a direction changing mechanism.

4. The device as claimed in claim 2 wherein said link mechanism comprises a direction transmitting mechanism which includes gears for coupling said first and second levers to each other.

5. The device as claimed in claim 2 wherein said link mechanism comprises a direction transmitting mechanism which includes frictional surfaces for coupling said first and second levers to each other.

6. The device as claimed in any of claims 2, 3, 4 and 5 further comprising a sleeve, a univeral joint, an operating lever, and a gimbal mechanism, said sleeve being slidable along the axial direction of said third lever and said sleeve being coupled through said univeral joint to said operating lever supported by said gimbal mechanism.

* * * * *